US012779073B2

(12) United States Patent
Fryer et al.

(10) Patent No.: US 12,779,073 B2
(45) Date of Patent: Nov. 3, 2026

(54) STERILIZATION ASSESSMENT METHODS WITH CHEMICAL INDICATORS

(71) Applicant: Advanced Sterilization Products, Inc., Irvine, CA (US)

(72) Inventors: Benjamin M. Fryer, Lake Forest, CA (US); Doug V. Truong, Irvine, CA (US); Raya Fryer, Lake Forest, CA (US)

(73) Assignee: Advanced Sterilization Products, Inc., Irvine, CA (US)

( * ) Notice: Subject to any disclaimer, the term of this patent is extended or adjusted under 35 U.S.C. 154(b) by 1147 days.

(21) Appl. No.: 17/442,944

(22) PCT Filed: Mar. 25, 2020

(86) PCT No.: PCT/IB2020/052832

§ 371 (c)(1),
(2) Date: Sep. 24, 2021

(87) PCT Pub. No.: WO2020/201933

PCT Pub. Date: Oct. 8, 2020

(65) Prior Publication Data

US 2022/0226528 A1 Jul. 21, 2022

Related U.S. Application Data

(60) Provisional application No. 62/826,694, filed on Mar. 29, 2019.

(51) Int. Cl.
*A61L 103/15* (2026.01)
*A61L 2/24* (2006.01)
(Continued)

(52) U.S. Cl.
CPC *A61L 2/28* (2013.01); *A61L 2/24* (2013.01); *G01N 31/226* (2013.01);
(Continued)

(58) Field of Classification Search
CPC .......................................................... A61L 2/28
See application file for complete search history.

(56) References Cited

U.S. PATENT DOCUMENTS 5,916,816 A 6/1999 Read
6,488,890 B1 12/2002 Kirckof
(Continued)

FOREIGN PATENT DOCUMENTS

CN 1151703 A * 6/1997 ............... A61L 2/28
CN 101513035 A 8/2009
(Continued)

OTHER PUBLICATIONS

DE-102005048968—Translation (Year: 2006).*
(Continued)

*Primary Examiner* — Sean E Conley
*Assistant Examiner* — Changru Chen
(74) *Attorney, Agent, or Firm* — Lerner David LLP

(57) ABSTRACT

A class 5 chemical indicator color may be imaged such that a color of the indicator may be determined and compared to a color-value threshold indicative of an efficacious sterilization procedure. Color changes of the indicator during a sterilization procedure are typically not uniform. As such, colors on the indicator may be averaged and then compared to the color-value threshold to determine if the procedure has been efficacious or if additional exposure to a sterilant may be desired. Color values and color-value thresholds may be based on, e.g., the L*a*b* color model or a grayscale color model.

20 Claims, 3 Drawing Sheets

(51) Int. Cl.
*A61L 2/28* (2006.01)
*G01N 31/22* (2006.01)

(52) U.S. Cl.
CPC ..... *A61L 2103/15* (2026.01); *A61L 2202/122* (2013.01); *A61L 2202/14* (2013.01)

(56) References Cited

U.S. PATENT DOCUMENTS

| | | | |
|---|---|---|---|
| 2008/0055616 A1 | 3/2008 | Scott et al. | |
| 2011/0275159 A1 | 11/2011 | Landgrebe et al. | |
| 2012/0021406 A1 | 1/2012 | Franciskovich et al. | |
| 2012/0230879 A1 | 9/2012 | Dunkley et al. | |
| 2013/0250322 A1* | 9/2013 | Kawabata ............ | H04N 1/6058 358/1.9 |
| 2015/0024501 A1 | 1/2015 | Lacy et al. | |
| 2017/0304476 A1 | 10/2017 | Taggart et al. | |
| 2020/0237939 A1 | 7/2020 | Henniges et al. | |

FOREIGN PATENT DOCUMENTS

| | | | | |
|---|---|---|---|---|
| CN | 101936912 A | 1/2011 | | |
| CN | 104263805 A | 1/2015 | | |
| CN | 108289971 A | 7/2018 | | |
| DE | 102005048968 A1 * | 4/2007 | ............... | A61L 2/28 |
| JP | H08-094530 A | 4/1996 | | |
| JP | H11-178598 A | 7/1999 | | |
| JP | 2003-505106 A | 2/2003 | | |
| JP | 2003-325646 A | 11/2003 | | |
| JP | 2007-218878 A | 8/2007 | | |
| JP | 2009-133634 A | 6/2009 | | |
| JP | 2010-096726 A | 4/2010 | | |
| JP | 2013-503813 A | 2/2013 | | |
| JP | 2018-064878 A | 4/2018 | | |
| JP | 2018-205208 A | 12/2018 | | |
| KR | 10-2017-0102828 A | 9/2017 | | |
| WO | 0110473 A1 | 2/2001 | | |
| WO | 2012012055 A2 | 1/2012 | | |
| WO | 2017044906 A2 | 3/2017 | | |

OTHER PUBLICATIONS

CN_1151703_A_Translation (Year: 1997).*
Australian Search Report for AU Application No. 2020254051, dated Sep. 26, 2024, 1 page.
PCT Written Opinion of the International Searching Authority of PCT/IB2020/052832 dated Jul. 8, 2020, 6 pages.
PCT International Search Report of PCT/IB2020/052832 dated Jul. 8, 2020, 5 pages.
PCT International Preliminary Report on Patentability of PCT/IB2020/052832 dated Sep. 28, 2021, 7 pages.

* cited by examiner

STERILIZATION ASSESSMENT METHODS WITH CHEMICAL INDICATORS

CROSS-REFERENCE TO RELATED APPLICATIONS

The present application is a U.S. National Phase Application of International Application No. PCT/IB2020/052832, filed Mar. 25, 2020, which claims priority to U.S. Provisional Patent Application No. 62/826,694, filed Mar. 29, 2019. The entire contents of these applications are incorporated by reference herein in their entirety.

FIELD

The subject matter disclosed herein relates sterilization indicators, particularly chemical indicators that may be used to assess the exposure of a sterilant during a chemical-vapor sterilization procedure.

BACKGROUND

Medical devices are typically sterilized before use in order to minimize the likelihood that a contaminated device might be used on a subject, which could cause an infection in the subject. Various sterilization techniques may be employed using various sterilizing fluids, often referred to as sterilants, such as steam, hydrogen peroxide, ethylene oxide (EtO), and vapor phase sterilization, either with or without a gas plasma. Each of these techniques depends to a certain extent on the diffusion rates of the sterilization fluids, typically gases, upon the medical devices to be sterilized.

Before sterilization, medical devices are typically packaged within containers or pouches having a semi-permeable barrier that allows transmission of the sterilant, but prevents admission of contaminating organisms, particularly post-sterilization and until the package is opened by medical personnel. For the sterilization cycle to be efficacious, the contaminating organisms within the package must be killed because any organisms that survive the sterilization cycle could multiply and re-contaminate the medical device.

Although the packaging helps prevent contamination of a sterile medical device, the packaging may increase the difficulty of achieving a successful sterilization cycle because the packaging impedes the sterilant from reaching the device or instrument contained therein. This is particularly problematic for devices and instruments that have diffusion-restricted spaces therein because these diffusion-restricted spaces reduce the likelihood that a sterilization cycle may be effective. For example, endoscopes typically have long narrow lumens into which the sterilant must diffuse in sufficient concentration for sufficient time to achieve a successful sterilization cycle.

Confirming that a sterilization cycle has been efficacious helps medical personnel avoid using a contaminated medical device on a subject. Typically, the sterilized medical device is not itself checked for contaminating organisms because such an activity would introduce other contaminating organisms to the medical device, thereby re-contaminating it. Thus, an indirect check has been developed in the form of a sterilization indicator.

A sterilization indicator is a device that may be placed alongside or in proximity to a medical device being subject to a sterilization cycle, such that the sterilization indicator is subject to the same sterilization cycle as the medical device. One type of sterilization indicator is a chemical indicator. Chemical indicators typically comprise a substrate or support upon which is disposed a chemical indicator composition (ink) for detecting an oxidizing agent, such as hydrogen peroxide, which achieves a distinct range of different color changes upon exposure to different doses of the oxidizing agent. Applicant, i.e., Advanced Sterilization Products ("ASP"), Division of Ethicon US, LLC, a Johnson & Johnson company, currently sells chemical indicators, such as the STERRAD® Chemical Indicator Strip, Part no. 14100.

Chemical indicators are classified according to intended applications according to ISO11140, from class 1 to class 6. Of relevance here are class 5 chemical indicators, which have performance comparable to biological indicators, such as ASP's commercially available STERRAD VELOCITY™ Biological Indicator, part no. 43210. The STERRAD VELOCITY™ Biological Indicator includes a class 5 chemical indicator adhered to an outer surface, which is currently used to provide a user with a quick indication of whether the BI has been exposed to hydrogen peroxide prior to subjecting the biological indicator to further analysis, which could take up to half an hour, or longer.

SUMMARY OF THE DISCLOSURE

Disclosed herein is a method of assessing an efficacy of a sterilization procedure performed by a sterilization apparatus comprising a chamber. The method comprises placing a chemical indicator in the chamber, commencing a sterilization procedure, obtaining an image of the chemical indicator using a digital imaging device, determining a color value of the image of the chemical indicator, comparing the color value to a color-value threshold, determining that the color value passed the color-value threshold, and automatically ending the sterilization procedure following a determination that the color value has passed the color-value threshold. The method may also include steps of placing an instrument in a non-sterile state in the chamber proximate to the chemical indicator before commencing the sterilization procedure, opening a door of the chamber after the sterilization procedure has ended, and removing the instrument in a sterile state from the chamber after the sterilization procedure has ended. Additionally, the method may further comprise a step of averaging the image of the chemical indicator to create an averaged image such that the step of determining the color value of the image comprises determining the color value of the averaged image.

Determination of color values may be based on, e.g., the L*a*b* color model or a grayscale color model. As such, the color value may comprise an a* value such that, as determined by the inventors, the color-value threshold may comprise an a* value between approximately −9 and 9, e.g., approximately 0. Further, the a* value may comprise a value greater than about 48 during the step of placing the chemical indicator in the chamber. Where color values are expressed in grayscale, the color value may comprise a K % value such that, as determined by the inventors, the color-value threshold may comprise a K % value between approximately 50% and 60% black, e.g., about 54%. Further, the K % value may comprise a value greater than about 61% during the step of placing the chemical indicator in the chamber.

Another method disclosed herein for assessing an efficacy of a sterilization procedure performed by a sterilization apparatus comprising a chamber includes steps of placing a chemical indicator in the chamber, commencing a sterilization procedure, obtaining an image of the chemical indicator using a digital imaging device, determining a color value of the image of the chemical indicator, comparing the color value to a predetermined color-value threshold, determining that the color value has not passed the color-value threshold, waiting for a dwell time, introducing a volume of sterilant into the chamber, obtaining a subsequent image of the chemical indicator using the digital imaging device, determining a subsequent color value of the subsequent image of the chemical indicator, determining that the subsequent color value of the subsequent image of the chemical indicator has passed the color-value threshold, and automatically ending the sterilization procedure following a determination that the subsequent color value has passed the color-value threshold. The method may further comprise placing an instrument in a non-sterile state in the chamber proximate to the chemical indicator before commencing the sterilization procedure, automatically opening a door of the chamber after the sterilization procedure has ended, and removing the instrument in a sterile state from the chamber after the sterilization procedure has ended.

The method may further comprise averaging the image of the chemical indicator to create an averaged image such that the step of determining the color value of the image comprises determining the color value of the averaged image. Additionally, the method may also comprise averaging the subsequent image of the chemical indicator to create a subsequent averaged image such that the step of determining the subsequent color value of the subsequent image comprises determining the subsequent color value of the subsequent averaged image. The color value and the subsequent color value may comprise, e.g., a* values or grayscale values. As such, the color value may comprise an a* value such that, as determined by the inventors, the color-value threshold may comprise an a* value between approximately −9 and 9, e.g., approximately 0. Further, the a* value may comprise a value greater than about 48 during the step of placing the chemical indicator in the chamber. Where color values are expressed in grayscale, the color value may comprise an K % value such that, as determined by the inventors, the color-value threshold may comprise a K % value between approximately 50% and 60% black, e.g., about 54%. Further, the K % value may comprise a value greater than about 61% during the step of placing the chemical indicator in the chamber.

Also disclosed is a method of operating a sterilization apparatus with the aid of a digital computer, the sterilization apparatus having a chamber and a digital imaging device. The method includes steps of providing the computer with a data base comprising color values according to the L*a*b* color space, placing a medical device in a non-sterile state and a chemical indicator into the chamber, placing a chemical indicator into the chamber proximate to the medical device, initiating an interval timer in the computer upon closure of the chamber for monitoring the elapsed time since the closure, repetitively obtaining an image of the chemical indicator using the digital imaging device, averaging each of the repeatedly obtained images of the chemical indicator, repetitively determining a color value for each of the averaged images, repetitively comparing each of the color values to a color-value threshold, repeatedly determining whether the color value has passed the color-value threshold, automatically ending the sterilization procedure following a determination that the color value has passed the color-value threshold, automatically opening the chamber, and removing the instruments in a sterile-state from the chamber.

In certain variations of this method, the color value may comprise an a* value or a K % value. As such, the color value may comprise an a* value such that, as determined by the inventors, the color-value threshold may comprise an a* value between approximately −9 and 9, e.g., approximately 0. Further, the a* value may comprise a value greater than about 48 during the step of placing the chemical indicator in the chamber. Where color values are expressed in grayscale, the color value may comprise an K % value such that, as determined by the inventors, the color-value threshold may comprise a K % value between approximately 50% and 60% black, e.g., about 54%. Further, the K % value may comprise a value greater than about 61% during the step of placing the chemical indicator in the chamber.

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like reference numerals identify the same elements and in which:

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

Figure 1:
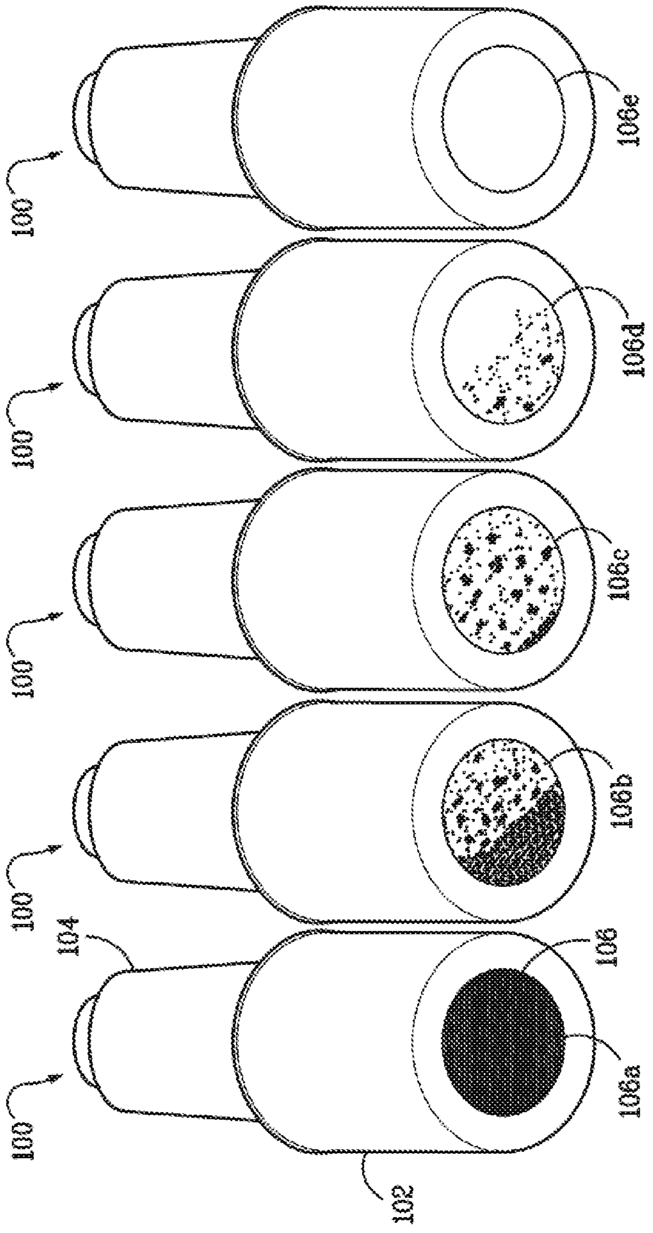
FIG. 1 depicts an assortment of biological indicators including chemical indicators that have been subject to different sterilization procedures.

FIG. 1 reflects a perspective view of five units of the STERRAD VELOCITY™ Biological Indicator 100 placed side by side. Each of these units includes a cap 102 and a vial 104. Affixed to each cap 102 is a class 5 chemical indicator 106. When a unit 100 is removed from its packaging, chemical indicator 106 is colored so as to indicate that the unit has never been in contact with a sterilant, such as hydrogen peroxide vapor. For example, the color red may be used to indicate that chemical indicator 106 has not been in contact with a sterilant. Although the commercial offering of the STERRAD VELOCITY™ Biological Indicator, which is used to describe the technological improvements herein, includes a chemical indicator that is sensitive to hydrogen peroxide, it should be understood that any class 5 chemical indicator may be used to practice the subject matter described herein, including independent of any biological indicator. Such class 5 chemical indicators may be sensitive to or change color when exposed to, e.g., steam, peracetic acid, ethylene oxide, or any other substance that may be used as a sterilant to kill microorganisms.

Biological indicator 100, including chemical indicator 106, may be exposed to a sterilant, e.g., hydrogen peroxide, typically during a sterilization procedure conducted by an automated sterilization system, which may be referred to as a sterilizer, such as ASP's STERRAD® System, STERRAD® NX System or STERRAD® 100NX System. Upon exposure to the sterilant, the color of indicator 106 may change from a first color (e.g., red) that indicates indicator 106 has not been exposed to the sterilant to a second color (e.g., yellow) that indicates indicator 106 has been exposed to the sterilant. Typically the change between these two colors is not instantaneous, but may be gradual, depending on characteristics of the exposure, such as exposure time and sterilant concentration. Furthermore the transition between the two colors may not occur uniformly over the surface of indicator 106. For example, patches of coloration may occur during the transition from the first color to the second color. As shown, indicators 160*a-e* show different degrees of color transition based on differing amounts of sterilant exposure. Indicator 106*a* is uniformly the first color (shown in black) whereas indicator 106*e* is uniformly the second color (shown in white). Indicators 106*b-d* show irregular color patches that may occur during the color-change transition when exposure to the sterilant is less than the exposure necessary to achieve a complete transition from the first color to the second color.

A human user may reliably determine whether biological indicator 100 has been exposed to a sufficient or desired amount of sterilant, e.g., hydrogen peroxide, when the transition from the first color to the second color is complete. However, such a determination may not be reliable when the color transition is partial. For example, in FIG. 1, the first color, e.g., red, is represented in black on chemical indicator 106, whereas the second color, e.g., yellow, is represented in white on chemical indicator 106. Chemical indictor 106*a* is uniformly the first color, indicating that it has not been exposed to a sterilant. Chemical indicator 106*e* is uniformly the second color, such that a human user should be able to determine form the chemical indicator alone that biological indicator 100 has been exposed to a sufficient or desired amount of sterilant, and to correspondingly determine that a sterilization procedure may have been efficacious. Chemical indicators 106*b-d* include various combinations of the first color and the second color, indicating that the transition from the first color (indicator 106*a*) to the second color (indicator 106*e*) was not complete, such that a human user might not be able to determine form the chemical indicator alone whether biological indicator 100 has been exposed to a sufficient or desired amount of sterilant. In these instances, a human user likely would determine that the sterilant exposure was insufficient such that the sterilization procedure was not efficacious even though it might have been. Applicant has thus developed a digital imaging and analysis technique that may be used improve the technology of assessing adequacy of a sterilization procedure by determining whether a partial color change, such as that of indicator 106*d*, indicates that biological indicator 100 has or has not been exposed to a sufficient or desired amount of sterilant, and whether a partial color change, such as that of indicator 106*b* or 106*c*, indicates that additional exposure to sterilant may be desired.

The digital imaging and analysis technique may be carried out according to various methods and variations, each of which includes at least the steps of obtaining an image of the chemical indicator, determining a color value of the image of the chemical indicator, comparing the color value to a color-value threshold, and determining that the color value passed the color-value threshold. The image of the chemical indicator may be obtained using a digital imaging device, such as a digital camera capable of taking a photograph of the chemical indicator. The image may then be input into a processor, e.g., a processor of the digital imaging device or of a digital computer, which may be independent from the digital imaging device. The processor may be configured to analyze the color(s) of the chemical indicator, e.g., by running thereon software, such as Adobe® Photoshop®. In particular, the color of the chemical indicator may be analyzed according to various color schemes, such as the L*a*b* color model ("Lab model") or a grayscale color model.

In the Lab model, colors are defined according to three perpendicular axes. The first axis is the L axis. Values on the lightness or L* axis indicate how much white to black may be present in an image or portion of an image, e.g., a pixel or collection of pixels. L* values typically range from 0 to 100, where 0 indicates darkest black and 100 indicates brightest white. Values on the a* axis indicate the amount of green to red, typically with −128 corresponding to pure green and 127 corresponding to pure red. Values on the b* axis indicate the amount of blue to yellow, typically with −128 corresponding to pure blue and 127 corresponding to pure yellow. In the grayscale model, colors are processed as though they comprise only black, white, or a combination thereof, similar to the L* value of the Lab model, except that in grayscale, 100% often refers to darkest black and 0% often refers to brightest white.

As such, the processor may process a color image of chemical indicator 106 and determine the L*, a*, and b* values in the Lab model. Alternatively or additionally, the processor may process the image to determine how black it is in the grayscale model. As noted, however, the chemical indicator 106 being analyzed may not have been subject to a sufficient amount of sterilant to change its color from the first color (e.g., red or black) to uniformly be the second color (e.g., yellow or white). In these instances, indicator 106 may include patches of the first color (e.g., a red corresponding to an a* of between about +48 and +127, which in grayscale correspond to a K % of about 61 to 100), patches of the second color (e.g., a yellow corresponding to an a* of between −128 and about 0, which in grayscale correspond to a K % of between 0 and about 54), and patches of colors in between the first color and second color (e.g., a light red or orange corresponding to an a* of between about 0 and about +48, which in grayscale correspond to a K % of between about 54 and about 76). The processor may thus compensate for the differing patches of color. One form of compensation may be called "blurring" or "averaging." For example, Adobe® Photoshop® includes a function called "Average Blur," which separately averages all of the L*, a*, and b* values, or grayscale percentage, for each pixel in an image or a portion of the image. Thus, for example, the a* value for each pixel may be summed and then divided by the total number of pixels to calculate an average a* value of the three patches.

This method of determining a color value for chemical indicator 106 may additionally be used to determine a color-value threshold upon which a determination of sufficient sterilant exposure may be based. This was accomplished by, first, subjecting a population of units of the STERRAD VELOCITY™ Biological Indicator to various sterilization cycles of the STERRAD® NX, STERRAD® 100NX, and STERRAD 100S such that sample sets of the units were exposed to different volumes of hydrogen peroxide for different times within the three systems. Specifically, in experiments performed by Applicant, five to ten units each were exposed to thirty nine combinations of hydrogen peroxide volume, exposure time, and system type, such that these units would either be incompletely sterilized or completely sterilized. In total, 340 units were tested. Second, for each biological indicator, color values (a* and grayscale) of each chemical indicator were then determined by: 1) taking a picture, i.e. digital image, of each chemical indicator using a digital camera; 2) opening each image in Adobe® Photoshop® CS6; 3) averaging each image of each chemical indicator using the Average Blur function; and 4) recording the a* value and grayscale value (referred to as K % in Adobe® Photoshop® CS6) reflected in the "Color" window when in, respectively, the L*a*b* color mode and grayscale color mode. Third, probability plots for a* and K % were created from data corresponding to the maximum injection volume for each of the cycles in each of the systems. These plots reflected that an a* value of less than 0 and a K % value of less than 54% would each provide a less than 1 in 10,000 chance that the chemical indicator was exposed to an insufficient amount of hydrogen peroxide to achieve sterilization. Accordingly, an a* of 0 and a K % value of 54% may be considered color-value thresholds such that a chemical indicator having an a* of less than approximately 0 or a K % of less than approximately 54% may be considered completely sterilized. If a lesser or greater reliability in the determination is desired, the color-value threshold may be adjusted. For example, if a greater reliability is desired, the color-value thresholds may be an a* of approximately −9 or a K % of approximately 50%. If a lesser reliability is desired, the color-value thresholds may be an a* of approximately 9 or a K % of approximately 60%.

Determination of the color value of chemical indicator 106, and whether the color value has passed the color-value threshold, may be performed after a sterilization cycle has been completed, such that comparison of the color value to the color-value threshold, and a sterilization determination based thereon, would also be performed after the sterilization cycle has been completed. A post-cycle sterilization determination of the chemical indicator may be an improvement over the current post-cycle sterilization determination based on assessment of a biological indicator because capturing an image of the chemical indicator, determining its color value, and comparing the color value to the color-value threshold may be accomplished more quickly than assessing a biological indicator. For example, assessment of the STERRAD VELOCITY™ Biological Indicator requires approximately thirty minutes, whereas assessment of the chemical indicator should require a five minutes or less to capture and analyze the image.

Figure 2:
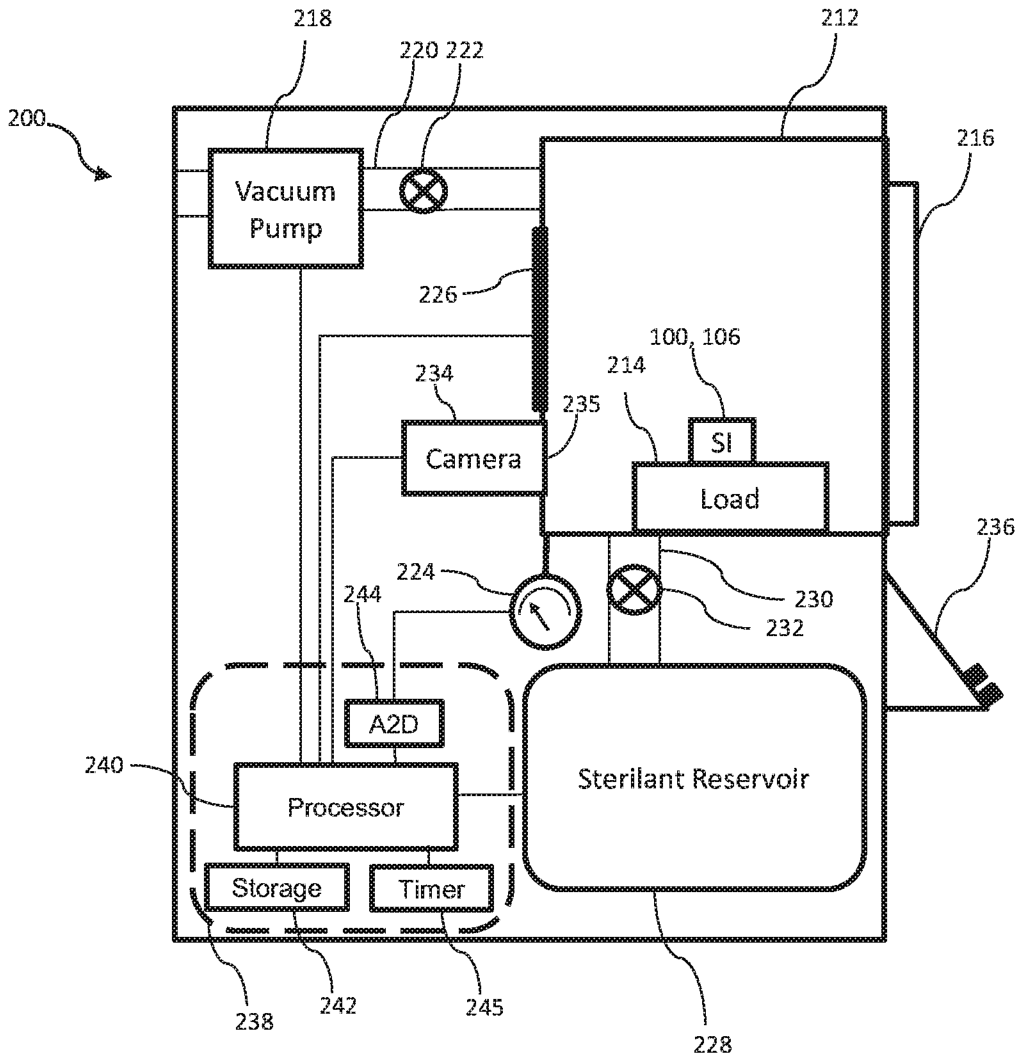
FIG. 2 depicts a schematic of a sterilization system.

Determination of the color value of chemical indicator 106, and whether the color value has passed the color-value threshold, may also be performed repetitively during a sterilization cycle by a sterilizer, such as the sterilizer 200 depicted schematically in block diagram format in FIG. 2. Sterilizer 200 comprises a chamber 212 having a load (pack) 214 of instruments therein to be sterilized. One or more sterilization indicators (i.e., biological indicator 100 having a chemical indicator 106, or a chemical indicator 106 separate from a biological indicator) may be disposed within chamber 212, such as placed upon or secured to load 214 as shown. The chamber 12 may be formed of any material that is sufficiently robust to handle pressures as low as approximately between 0.3 torr and 3 torr, and sufficiently inert to avoid reacting with or absorbing any sterilants introduced therein. Such materials may include aluminum and stainless steel. Chamber 212 may also include an openable and sealable barrier 216, such as a door, that may be opened to allow placement and removal of load 214 into chamber 212. The barrier should be sufficiently robust, and include a sufficiently robust seal, to withstand low pressures drawn within chamber 212 and avoid leaks between chamber 212 and the ambient environment. A vacuum pump 218 capable of reaching the desired operating pressure evacuates air and other gases, such as water vapor, from chamber 212. Vacuum pump 218 may include a hose or pipe 220 to connect it to chamber 212. Vacuum pump 218 may also include a valve 222, which may be open or closed to assist or prevent pressure changes in chamber 212. For example, when the valve is open and the vacuum pump is operational, the pressure in chamber 212 may be lowered. Alternatively, when the valve is open and the vacuum pump is not operational, the pressure in the chamber may be equalized to the ambient pressure. In other embodiments, a valve that is not part of vacuum pump 218 may be used to control whether chamber 212 has a pressure equal to the ambient pressure. A pressure monitor 224 monitors the pressure in chamber 212. Particularly suitable pressure monitors are capacitance manometers available from MKS Instruments. A heating element 226 may be used to heat the chamber 212. It may comprise separate elements bonded to the outside of the chamber 212 in locations sufficient to uniformly heat the chamber 212. A tank or reservoir 228 containing sterilant, which includes a hose or pipe 230, is connected to chamber 212. In some embodiments, tank 228 may further include a valve 232, which may be disposed between chamber 212 and tank 228 to control the flow of sterilant from tank 228 through hose 230 and into chamber 212. An imaging device, such as a camera 234, may be disposed alongside a viewing window 235 of chamber 212 for capturing images of chemical indicator 106. A power source and/or signal generator and an electrode (not shown) disposed within chamber 212 may be provided to create an electric field within chamber 212 between the electrode and the interior surface of chamber 212 to create a plasma therein. Creation of a plasma is useful for low temperature sterilization processes that use hydrogen peroxide gas. In these processes, the hydrogen peroxide gas may be excited to form a hydrogen peroxide plasma. Alternatively, another gas may be used to form the plasma, such as air, which may help lower hydrogen peroxide residuals upon the load to facilitate removal of hydrogen peroxide from chamber 212. Sterilization system 200 may also include a user interface 236, that may include output devices, such as a printer or display, and user-input devices, such as a keypad or touch screen.

A control system 238, such as a digital computer, controls the operation of sterilizer 200 and its various components. Control system 238 may employ one or more microprocessors 240. It may also employ a non-transitory storage medium 242, such as random access memory (RAM), a hard-disk drive, or flash memory, which can store data, such as color values (e.g., a data base comprising color values according to the Lab color model and a grayscale color model) and color-value thresholds. An analog to digital (A2D) converter 244 may be used to convert analog data to digital data if analog data, such as pressure data, is collected. A timer or clock circuit 245 keeps time. Control system 238 may further include software and/or logic by which microprocessor 240 may repetitively activate camera 234 to capture and store images of chemical indicator 106 in storage medium 242, analyze the images to determine a color value of the chemical indicator, compare color values to the color-value thresholds, and determine whether a color value has passed a color-value threshold. Alternatively, sterilizer 200 may include an input/output port such that an external digital computer may provide this software and/or logic, e.g., by including thereon software, such as Adobe® Photoshop® CS6, capable of determining color value, and outputting these values back to processor 240.

Figure 3:
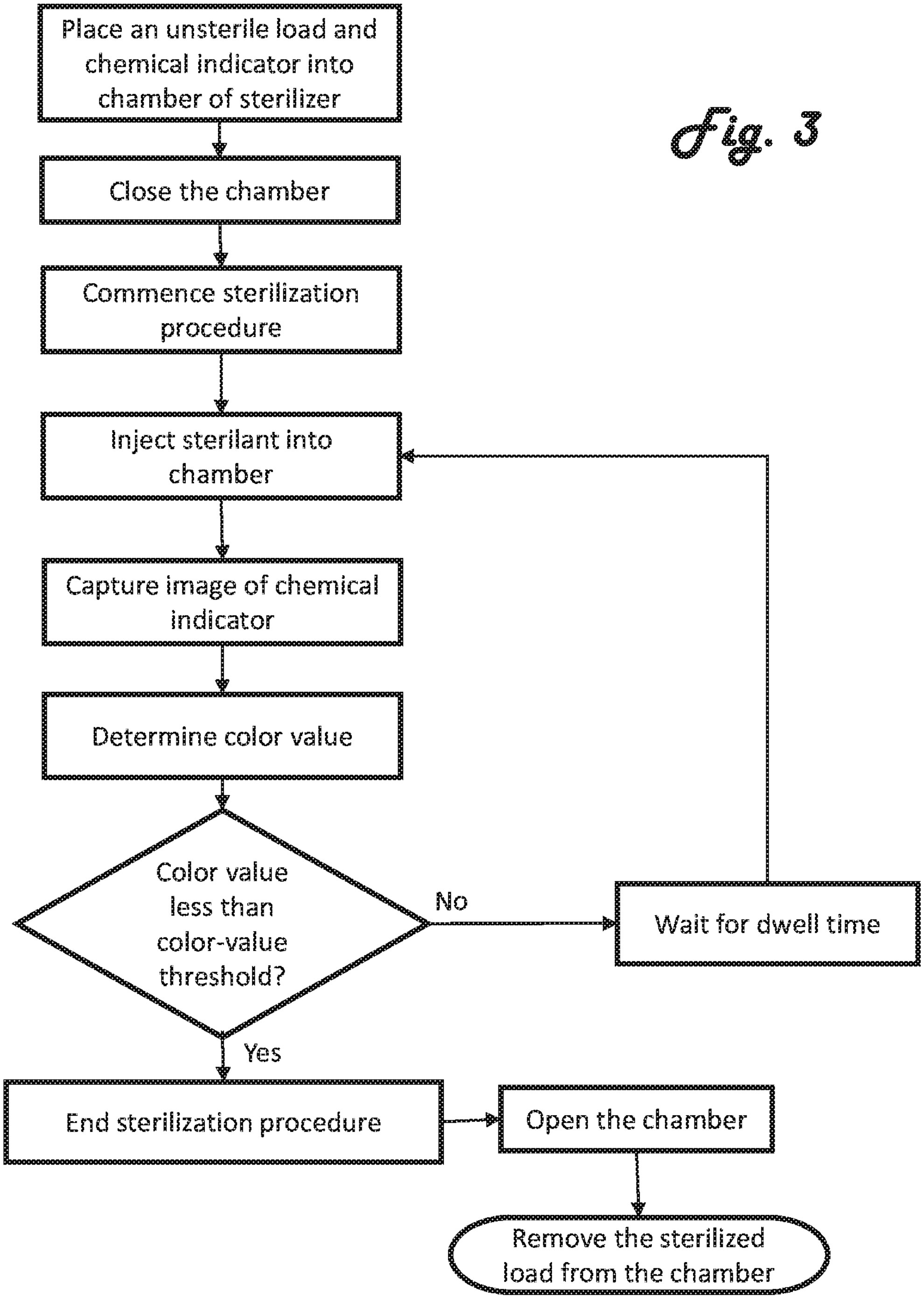
FIG. 3 depicts a flow chart reflecting an operating procedure for the sterilization system of FIG. 2.

Processor 240 may be configured to automatically end a sterilization process upon determining that a color value has passed a color value-threshold. Alternatively or additionally, processor 240 may be configured to wait for a dwell time, automatically introduce a volume of sterilant from sterilant reservoir 228 into chamber 212, or both upon determining that a color value has not passed a color-value threshold By virtue of the technology illustrated and described herein, and with reference to FIG. 3, Applicant has devised a method and variations thereof for assessing an efficacy of a sterilization procedure performed by a sterilizer comprising a chamber. The method begins by placing a chemical indicator into the chamber. The chemical indicator may be affixed to a biological indicator or it may be independent of a biological indicator. For example, the chemical indicator may be placed into the chamber with or without a biological indicator. Preferably, a STERRAD VELOCITY™ Biological Indicator, which includes a chemical indicator, is placed into the chamber. The chemical indicator may be placed proximate to a load of instruments, e.g., medical devices, such as an endoscope, in the sterilization chamber. A door of the sterilizer may be closed such that the sterilization procedure may be commenced. During the sterilization procedure, a volume of a sterilant may be introduced, e.g., injected into the chamber to expose the chemical indicator and load to the sterilant. An imaging device, such as a camera, may then obtain an image of the chemical indicator. Next a color value of the image of the chemical indicator may be determined. This color value may be compared to a color-value threshold in order to determine whether the color value has passed the color-value threshold. If the color value has not passed the color value threshold, the processor may wait for a dwell time, e.g., approximately thirty seconds, approximately one minute, approximately two minutes, or approximately five minutes before continuing the procedure. Additionally or alternatively, the processor may cause an additional volume of sterilant to be introduced into the chamber after the dwell time. In certain variations of the method, the processor may not wait for a dwell time before injecting additional sterilant into the chamber, such that the dwell time may be considered zero seconds. After the dwell time or additional sterilant has been injected, a subsequent image may be obtained such that a subsequent color value of the subsequent image may be determined. This subsequent color value may then be compared to the color-value threshold in order to determine whether the subsequent color value has passed the color-value threshold. If not, the foregoing steps of waiting for a dwell time (which, again, is optional), introducing an additional volume of sterilant, obtaining a subsequent image, determining a subsequent color value, and determining whether the color value has passed the color-value threshold may be repeated until the subsequent color value has passed the color value threshold. Upon such determination, the sterilization procedure may be ended, e.g., automatically, by the processor. In certain variations of the method, the processor may automatically open a door of the chamber.

Typically, the load placed into the chamber with the chemical indicator comprises medical devices in a non-sterile state. Therefore, after the sterilization procedure has been ended, the medical devices may be removed from the chamber in a sterile state.

In further variations of the method, determination of the color values and subsequent color values may include a step of averaging the image of the chemical indicator to create an averaged image such that the steps of determining these color values includes determining the color values of the averaged images.

In some variations of the method, the color value comprises an a* value of the Lab color model. In these variations, the color-value threshold value comprises an a* value between approximately −9 and 9, such as approximately 0. In other variations of the method, the color value comprises a grayscale value. In these variations, the color-value threshold comprises a grayscale value between approximately 50% to approximately 60% black, such as approximately 54%.

Any of the examples or embodiments described herein may include various other features in addition to or in lieu of those described above. The teachings, expressions, embodiments, examples, etc., described herein should not be viewed in isolation relative to each other. Various suitable ways in which the teachings herein may be combined should be clear to those skilled in the art in view of the teachings herein.

Having shown and described exemplary embodiments of the subject matter contained herein, further adaptations of the methods and systems described herein may be accomplished by appropriate modifications without departing from the scope of the claims. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

We claim:

1. A method, comprising:

obtaining an image of a chemical indicator associated with a load to be sterilized in a sterilization procedure;

determining an averaged color value of the image of the chemical indicator;

assessing an efficacy of the sterilization procedure based on a comparison of a color-value threshold and the averaged color value of the image of the chemical indicator; and automatically ending the sterilization procedure following a determination that the averaged color value passed the color-value threshold.

2. The method of claim 1, further comprising automatically opening a door after the sterilization procedure has ended.

3. The method of claim 1, further comprising averaging the image of the chemical indicator to create an averaged image such that determining the averaged color value of the image comprises determining a color value of the averaged image.

4. The method of claim 1, wherein the averaged color value comprises an a* value.

5. The method of claim 4, wherein the color-value threshold comprises an a* value between approximately −9 and 9.

6. The method of claim 5, wherein the color-value threshold comprises an a* value of approximately 0.

7. The method of claim 1, wherein the averaged color value comprises a grayscale value.

8. The method of claim 7, wherein the color-value threshold comprises a grayscale value that is between approximately 50% and approximately 60% black.

9. The method of claim 8, wherein the color-value threshold comprises a grayscale value of approximately 54%.

10. The method of claim 1, further comprising waiting for a dwell time following a determination that the averaged color value has not passed the color-value threshold.

11. A method, comprising:

obtaining an image of a chemical indicator associated with a load to be sterilized in a sterilization procedure;

determining an averaged color value of the image of the chemical indicator;

assessing an efficacy of the sterilization procedure based on a comparison of a color-value threshold and the averaged color value of the image of the chemical indicator; and waiting for a dwell time following a determination that the averaged color value has not passed the color-value threshold.

12. The method of claim 11, further comprising automatically ending the sterilization procedure following a determination that the averaged color value passed the color-value threshold.

13. The method of claim 11, further comprising automatically opening a door after the sterilization procedure has ended.

14. The method of claim 11, further comprising averaging the image of the chemical indicator to create an averaged image such that determining the averaged color value of the image comprises determining a color value of the averaged image.

15. The method of claim 11, wherein the averaged color value comprises an a* value.

16. The method of claim 15, wherein the color-value threshold comprises an a* value between approximately −9 and 9.

17. The method of claim 16, wherein the color-value threshold comprises an a* value of approximately 0.

18. The method of claim 11, wherein the averaged color value comprises a grayscale value.

19. The method of claim 18, wherein the color-value threshold comprises a grayscale value that is between approximately 50% and approximately 60% black.

20. The method of claim 19, wherein the color-value threshold comprises a grayscale value of approximately 54%.

* * * * *